United States Patent [19]

Wagenknecht

[11] Patent Number: 4,601,797
[45] Date of Patent: Jul. 22, 1986

[54] ELECTROCHEMICAL CARBOXYLATION OF p-ISOBUTYLACETOPHENONE AND OTHER ARYL KETONES

[75] Inventor: John H. Wagenknecht, Kirkwood, Mo.

[73] Assignee: Monsanto Company, St. Louis, Mo.

[21] Appl. No.: 707,260

[22] Filed: Mar. 1, 1985

Related U.S. Application Data

[63] Continuation-in-part of Ser. No. 683,542, Dec. 19, 1984.

[51] Int. Cl.[4] ............................ C25C 1/00; C25D 3/00
[52] U.S. Cl. .................................. 204/59 R; 548/444; 560/59; 560/60; 562/469; 562/470; 562/472
[58] Field of Search ...................... 204/59 R; 548/444; 560/59, 60; 562/470, 469, 472

[56] References Cited

U.S. PATENT DOCUMENTS

4,304,931 12/1981 Nicholson ........................... 562/469

OTHER PUBLICATIONS

Ikedo et al., Chemistry Letters, the Chemical Society of Japan, No. 3. Mar. 1984, pp. 453–454.

*Primary Examiner*—John F. Niebling
*Attorney, Agent, or Firm*—Joseph D. Kennedy; James W. Williams, Jr.; Arnold H. Cole

[57] ABSTRACT

Hydroxyibuprofen is produced in good yield by reduction of p-isobutylacetophenone at the cathode in the presence of carbon dioxide. Hydroxyibuprofen is readily hydrogenolyzed to ibuprofen. Electrochemical carboxylation of other selected aryl methyl ketones is also effected.

21 Claims, No Drawings

ELECTROCHEMICAL CARBOXYLATION OF p-ISOBUTYLACETOPHENONE AND OTHER ARYL KETONES

This application is a continuation-in-part of my application Ser. No. 683,542, filed Dec. 19, 1984.

The present invention relates to electrochemical carboxylation of substituted aryl methyl ketones, particularly to carboxylation of certain ketones, such as 4-acetoxyisobutylbenzene, which result in intermediates convertible to 2-arylpropionic acids having useful therapeutic properties.

It has previously been known that some types of organic compounds are subject to reduction at the cathode. It has also been known that some relatively stable reduction intermediates, such as in the case of benzalacetone, will react with carbon dioxide to form carboxyl compounds; see Wawzonek et al, Polarographic Studies in Acetonitrile and Dimethylformamide, J. Electrochem. Soc., Vol. 111, pages 324 to 328 (1964). However, acetophenones have been reported to give only very low to trace yields of hydroxy propionic acids, namely 2-hydroxy-2-phenyl propionic and 2-hydroxy-2-(p-methoxyphenyl) propionic acid; see Wawzonek et al, Polarographic Studies in Acetonitrile and Dimethylformamide, J. Electrochemical Society, 107, 537 (1960); also acetophenone has been reported to give a moderate yield of 2-hydroxy-2-phenyl-2-propionic acid in European patent application No. 0028430, Oct. 20, 1980.

The compound 2-(p-isobutylphenyl)propionic acid, known as ibuprofen, is a recognized, useful analgesic compound. There are a number of procedures for preparing this compound, but an improved route to the compound or improved methods of preparing its precursors would be useful. It has been known heretofore that 4-acetylisobutylbenzene can be obtained by aluminum chloride catalyzed reaction of isobutylbenzene with acetyl chloride, and that isobutyl benzene can be obtained by alkali catalyzed addition of propylene to toluene. Also a number of other substituted phenyl propionic acids are known to have analgesic properties; see U.S. Pat. Nos. 4,188,491; 3,385,886; 4,304,931, and 4,150,031. Preparations for particular propionic acid compounds have been described, including routes which involve 2-hydroxy-2-acyl propionic acids as intermediates.

SUMMARY OF THE INVENTION

The present invention involves the electrolytic carboxylation of certain aryl methyl ketones where the aryl group is of structure like that found in certain 2-arylpropionic acids of pronounced analgesic properties, as illustrated below, to obtain corresponding 2-aryl-2-hydroxypropionic acids or their ester or salt or amide derivatives. The overall reaction can be represented:

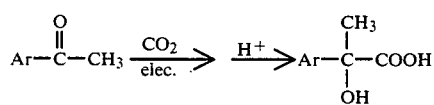

where Ar is selected from p-isobutylphenyl, 6-chlorocarbazyl-2, 3-phenoxyphenyl, 2-isopropylindanyl-5, 2-fluoryl, 2-fluoro-4-biphenylyl-, and 6-methoxynaphthyl-2.

The invention further involves the 2-step process of preparing such compounds and converting them, as by hydrogenolysis, to the corresponding arylpropionic acid.

In a particular aspect, the invention involves use of a dissolving anode to cause product precipitation, thereby providing a convenient separation technique.

The present invention is particularly exemplified by the electrolytic carboxylation of 4-acetylisobutylbenzene at the cathode to obtain 2-hydroxy-2-(p-isobutylphenyl) propionic acid or its ester or salt or amide derivatives.

DETAILED DISCLOSURE

The process involves effecting a reduction at the cathode of an electrolysis cell in the presence of carbon dioxide to effect carboxylation and can be illustrated by carboxylation of the 4-acetyl-isobutylbenzene. The carboxylation product can be converted to 2-hydroxy-2-(p-isobutylphenyl) propionic acid or its ester or salt derivatives for product recovery. The reaction is generally carried out in an electrolysis medium comprising an organic solvent and supporting electrolyte.

The reaction can be represented:

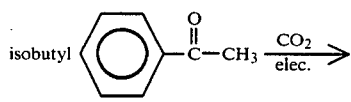

I

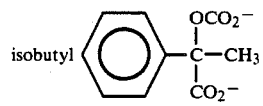

II

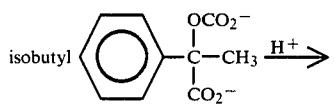

II

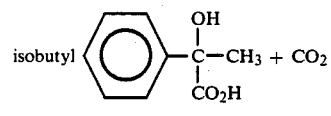

III

If an alkyl halide is present, or if the catholyte is treated with alkyl halide, e.g. methyl chloride, compound II or other derivative can be converted to the ester of III,

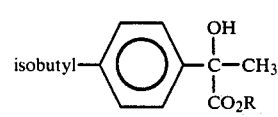

in which R is an alkyl group. Also, some of the cations present in the catholyte, or added in recovery or other procedures, may form salts of compound III,

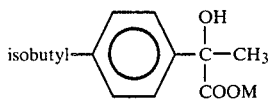

in which M is a salt forming cation. Ester of III can also be formed from decomposition of quaternary ammonium ions used as electrolyte, resulting in one of the organic radicals from the quaternary ammonium ion esterifying III. The salts, esters and acids of III are readily interconvertible so the present process will be useful regardless of the particular acid, ester or salt derivative of III which is produced. Thus the process can be used to prepare 2-hydroxy-2-(p-isobutylphenyl) propionic acid or derivatives in which —COOM in the above formula represents a group in which M is hydrogen, a salt-forming cation, or an esterifying group such as a monovalent hydrocarbyl radical.

The 2-hydroxy-2(p-isobutylphenyl)propionic acid, III, can be readily hydrogenolyzed to ibuprofen, IV:

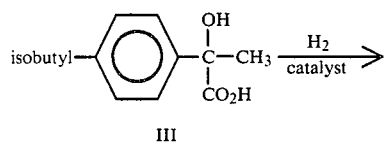

III

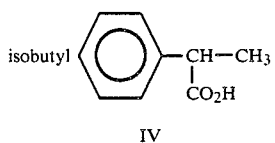

IV

Since compound III, 2-hydroxy-2(4-isobutylphenyl) propionic acid, differs from IV, 2-(4-isobutylphenyl) propionic acid, or ibuprofen, by a hydroxy substituent, compound III is at times named herein as hydroxyibuprofen and that name when used herein designates compound III.

In the present process the various other acyl methyl ketones disclosed herein can be converted to corresponding hydroxypropionic acids and hydrogenolyzed to corresponding propionic acids.

Thus, 2-acetyl-6-methoxynaphthalene is converted to 2-(6-methoxynaphthyl-2)-2-hydroxypropionic acid, which can be referred to as hydroxynaproxen.

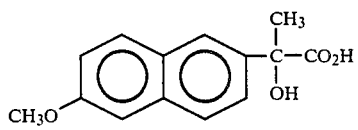

The compound can be hydrogenolyzed to naproxen, i.e. 2-(6-methoxy-naphthyl-2)-propionic acid.

The compound 2-acetylfluorene can be converted to 2(fluoryl-2)-2-hydroxypropionic acid, which can be termed hydroxycicloprofen:

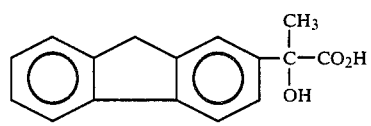

The compound can be hydrogenolyzed to 2-(fluoryl-2')propionic acid, i.e. cicloprofen.

The compound 2-isopropyl-5-acetylindane can be converted to 2-isopropyl-α-hydroxy-α-methylindan-5-acetic acid which can be called hydroxyisoprofen:

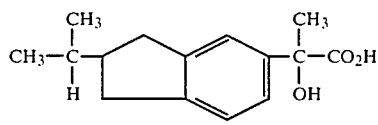

The compound can be hydrogenolyzed to 2-isopropyl-α-methylindan-5-acetic acid, i.e. isoprofen.

The compound 3-acetyldiphenyl ether can be converted to 2-(3-phenoxypheny)-2-hydroxypropionic acid, which can termed hydroxyfenoprofen:

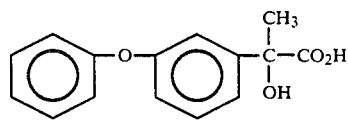

The compound can be hydrogenolyzed to 2-(3-phenoxyphenyl)propionic acid, i.e. fenoprofen.

The compound 2-acetyl-6-chlorocarbazole can be converted to 6-chloro-α-hydroxy-α-methylcarbazole-2-acetic acid, which can be called hydroxycarprofen:

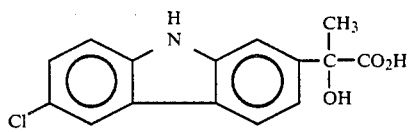

The compound can be hydrogenolyzed to 6-chloro-α-methylcarbazole-2-acetic acid, i.e. carprofen.

The compound 2-fluoro-4-acetylbiphenyl can be converted to 2-(2-fluoro-4-biphenylyl)-2-hydroxypropionic acid, which can be called hydroxyflurbiprofen.

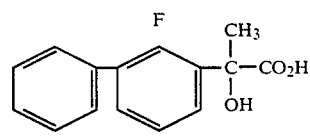

The compound can be hydrogenolyzed to 2-(2-fluoro-4-biphenylyl)propionic acid, i.e. flurbiprofen.

The hydrogenolyzed propionic acid componds from the above described conversions are all recognized therapeutic compounds, in particular having analgesic properties similar to those of aspirin. The reducibility at the cathode of particular reactants will vary from that of acetophenone depending upon the substituents on the benzene ring, or the fused ring structures involved. In general electron-donating substituents will make the reduction more difficult. Moreover, with naphthalene, some interfering reduction at nuclear carbon atoms might have been expected. In order to obtain the desired carboxylations, it appears necessary to obtain reduction on the acetyl moiety at potentials which can be obtained in the presence of carbon dioxide, which is also reducible at the cathode. The reactants in the conversions described above are set forth as suitable for electrochemical carboxylations to hydroxypropionic acid derivatives in accord with the present invention. In general conditions will be used as described in the illustrative examples with p-isobutylacetophenone and other acetylbenzene compounds.

The present process is capable of achieving good yields of hydroxyibuprofen with yields generally better than 50% and often up to 80 or 90% or higher, based upon p-acetylisobutylbenzene reacted.

In the description above, the reaction is indicated as involving a compound II:

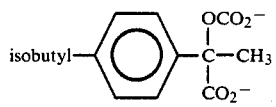

However, it may be that the reaction does not proceed through this compound, or that other routes are also involved in the conversion to hydroxyibuprofen or its derivatives. The process involves a reduction at the cathode and carboxylation of the isobutylphenylacetophenone by the carbon dioxide present, with production of a compound which involves, or can be converted to, hydroxyibuprofen or its salt or ester derivatives. The desired hydroxyibuprofen can be obtained, regardless of what the particular mechanism or intermediate may be. Therefore it is to be understood that the applicant is not limited to any particular mechanism for the reaction. As described and illustrated hereinbelow, a number of different procedures can be employed in recovering hydroxyibuprofen or its derivatives from the electrolysis reaction medium. The term "carboxylation" is used herein as general term to designate addition of or reaction with, carbon dioxide.

Also, it appears that producing the compound II above involves uptake of two electrons. It follows that the cathode voltage should be sufficiently negative to effect addition of the two electrons, although it is probable that an intermediate is formed which facilitates addition of the second electron. However, regardless of the actual reduction and the compound produced, the desired reaction will occur under the conditions described herein with the described supporting electrolytes. Thus, effective electrochemical reaction is obtained at the indicated range of cathode potentials.

In the present process, acidification has been found useful, as described hereinbelow, in treatment of reaction product and for recovering hydroxyibuprofen in free acid form. The acid treatment is useful regardless of whether the mechanism actually involves conversion of a bicarbonate group to a hydroxy group as illustrated in the conversion of compound II to compound III above. Gas evolution was generally observed upon acidification, but the illustrated reaction, which produces carbon dioxide, is not the only possible cause of gas evolution in the reaction system.

The electrolytic carboxylation reaction of the present invention can be effected under usual conditions for effecting reductive reactions of organic compounds at the cathode. The electrolysis is carried out by passing an electric current through a solution of the isobutylacetophenone in the presence of carbon dioxide. Procedures for effecting electrochemical reactions of organic compounds are well-documented in the literature and such procedures can be employed in the present process. In particular, procedures for effecting electrochemical reactions in nonaqueous solvents are generally suitable and can be used, see those described in Experimental Electrochemistry for Chemists, Sawyer and Roberts, John Wiley and Sons, (1974), with particular reference to Chapter 4, Solvents and Electrolytes, and the nonaqueous solvents at pages 203-210. In order to obtain good solubility of the ketone reactant, it is desirable to use an organic solvent. As most organic solvents have poor conductivity, the use of electrolytes is indicated, generally referred to as supporting electrolytes. As supporting electrolyte, it is generally preferred to employ those which will not undergo an interfering discharge under the electrolysis conditions. In the present invention this primarily concerns discharge at the cathode as the desired reaction occurs at the cathode, and suitable electrolytes are described in the above referred-to Sawyer and Roberts text. In particular, quanternary ammonium salts are generally preferred as quaternary ammonium ions generally have sufficiently negative discharge potentials to avoid interference in contemplated reactions. Thus tetrabutyl ammonium perchlorate, iodide, bromide, chloride, etc., can be used, tetraethylammonium perchlorate, tetraethylammonium chloride, and other tetraalkylammonium iodides, bromide, tetrafluoroborates, etc. The tetrabutylammonium salts, particularly the iodide and perchlorate, are often conveniently available and have good solubility in organic solvents. The anion does not take part in the desired reaction, so anions in general can be used, such as those of common acids. As discussed herein, water affects the present reaction, and it happens that some tetraethylammonium salts are more difficult to obtain in appropriate dry condition than some of the other quaternary ammonium salts. Various other amine and quaternary ammonium salts can be employed, such as those in commonly assigned U.S. Pat. No. 4,028,201 concerning electrolytic monocarboxylation of activated olefins. It is preferred to use supporting electrolyte salts of more negative discharge potential than that involved in the present reductive carboxylation which, depending upon electrode and conditions, may be in the range of about $-1.8$ to $-2.1$ volts vs the saturated calomel electrode. Alkali metal and other salts which discharge at less negative potentials are expected to undergo interfering discharge and to give poor results.

In the present process, water or moisture is deleterious. It has been found that the presence of water contributes to undesirable side reactions, with one of the products apparently being a dimer derivative of the starting ketone reactant. The present process is appropriately conducted in nonaqueous solvents, and particularly in those classed as polar or dipolar aprotic solvents as described on page 203 of the above referred-to Sawyer and Roberts text, particularly including acetonitrile, dimethylformamide and dimethyl sulfoxide, which are referred to, along with propylene carbonate, as the most widely used solvents. For economic reasons it is desirable to use a solvent of a fairly high dielectric constant in order to lower electrical resistance, without undue dependence on high concentrations of electrolyte salt, and the aprotic salts class to which acetonitrile and dimethylformamide belong in Table 4-5 of the Sawyer and Roberts text is shown as having a dielectric constant over 25. Acetonitrile and dimethylformamide are both reported as having a dielectric constant of 37 in the text, and both are good solvents.

The present electrolytic reaction can be conducted in the various types of electrolysis cells known to the art. In general such cells comprise a container made of material capable of resisting action of electrolytes, e.g.

glass or plastics, and a cathode and anode which are electrically connected to a source of electric current. Some anode materials are relatively inert and will have little or no influence on the course of electrolysis, and can be selected so as to minimize expense and any corrosion or erosion problem. Platinum and carbon are frequently used in the laboratory. Other electrode materials in general can be used as anodes, e.g. lead and lead alloys and oxides. Any suitable material can be employed as cathode, various metals, alloys, graphite, etc. being known to the art. In general, the art-recognized cathodes can be employed. Among the materials, some of the most popular are indicated to be mercury, lead, tin, copper, iron, aluminum, platinum, nickel and carbon; see Organic Electro-chemistry, edited by Baizer and Lund, Second Edition (1983), Marcel Dekker, Inc., N.Y., N.Y., page 182. With some electrolyses there is a preference for cathode materials of high hydrogen over-voltage, such as mercury, lead and cadmium, and such cathodes will be suitable in the present process. However, hydrogen generation is not a significant problem in nonaqueous media and other cathode materials can be suitably employed in the present process. Copper, for example, is very effective, and metal and carbon electrodes in general can be used.

In the present process, as in other electrolytic reactions, there is a possibility of interference between reactions at the cathode and anode. Thus, if a halide electrolyte is used, e.g. a bromide, bromine can be produced at the anode and if the bromine migrates to the cathode, it can be reduced, thereby lowering current efficiency. If an unsaturated compound is provided to take up the bromine, it or the resulting bromide, can react with cathode reduction products, thereby interfering with desired reactions. It is possible to conduct the desired carboxylation in an undivided cell, and some of the adverse effects can be lessened by selection of suitable salts or other material for an anode oxidation. Thus, an oxalate salt can be used, in a manner similar to that found successful in converting acetophenone to the corresponding 2-hydroxy propionic acid in a undivided cell using a quaternary ammonium oxalate electrolyte; see Angew, Chem. Int. Ed. Engl. 22, 492 (1983); Angew Chem. Suppl. 1983, 691–702; European patent application No. 0028430, Oct. 20, 1980. Good results can also be obtained if a divided cell is employed with a separator to prevent the free flow of components between the cathode and anode. A mechanical barrier can be used which has some permeability, e.g., a fritted glass filter, glass cloth, asbestos, porous vinyl chloride, etc. It is generally better to employ a selective membrane, such as an ion exchange membrane, particularly permselective cation exchange membranes which selectively permit migration of cations. Such membranes as described in commonly assigned Baizer et al U.S. Pat. No. 3,193,480 can suitably be employed. Suitable membranes are often characterized by having sulfonyl groups on a relatively impermeable polymeric material which is inert to and resistant to degradation by the electrolysis medium.

As a particular feature of the process, a dissolving anode may be used deliberately to introduce ions which cause the hydroxyibuprofen to precipitate thus providing a convenient separation technique. For example, it has been shown that Al anodes dissolve in this type of system and would probably cause the product to precipitate.

The dissolving anode is also useful in providing a material to be oxidized at the anode so that chlorine or other interfering materials are not generated in interfering amounts, which is particularly advantageous when an undivided cell is employed. Thus, it is a particular aspect of the present process to carry out the electrolysis with an oxidizable anode which is oxidized with dissolution to form metal ions under the electrolysis conditions, producing metal salts of the hydroxyibuprofen and intermediates and other products, which precipitate from the electrolysis medium. The precipitate materials can be readily separated and then acidified and extracted with organic solvents or otherwise treated to isolate the hydroxyibuprofen and other products. The product recovery is greatly facilitated by the direct precipitation of the product salt from the electrolysis medium. This precipitation avoids a number of steps which would otherwise be necessary for product recovery. In particular, it avoids any need to distill or otherwise remove the solvent, or to separate the electrolyte salts from the electrolysis medium, thereby making feasible the direct recycle of the electrolysis medium, after product removal by filtration, with any unreacted 4-acetylisobutylbenzene. This direct recycle will be advantageous for both batch and continuous processes. The removal of product by precipitation also has the advantage of avoiding further interfering reactions with the product, especially when an undivided cell is used, although that is not generally a significant problem with hydroxyibuprofen. Some of the advantages of the dissolving electrode can be obtained with a divided cell, using a cation exchange membrane so that the metal cations can migrate to the catholyte to form salts with the product. However, there will generally be little reason to use a divided cell when a dissolving electrode is used. For the dissolving electrodes, metals which are oxidizied and dissolved under the electrolysis conditions are suitable, and particularly those which form salts with the products which are relatively insoluble in the electrolysis medium, so as to effect a separation of product salts. Aluminum and iron have been found particularly suitable as dissolving electrodes.

it is also possible to cause precipitation of hydroxyibuprofen metal salts by simply having appropriate metal salts present in the electrolysis medium, e.g., aluminum chloride or other aluminum or iron halide or other salts. However, such use would not achieve the purpose of avoiding generation of halogen or other possibly interfering products at the anode and might also involve more expensive material than use of dissolving metal anodes. Such metal salts can be used with a divided cell with some potential advantages in separation, or can be used in conjunction with dissolving anodes of the same or different metals than that of the salts.

The use of dissolving electrodes and removal of product by precipitation will be useful in general in the electrocarboxylation of

compounds as described herein, in the same manner as in the preparation of hydroxyibuprofen. In fact, costs of product separation prior to recycling electrolyte are one of the major problems in such electrolytic precesses, probably being a bigger factor than the problems with divided cells referred to in the Angew. Chem. and related citations cited hereinabove; and the use of dissolving electrodes as described herein affords the opportunity for a very efficient product separation.

The electrolysis cells used in the examples herein are suitable for the present process, although the H-cell utilized in many of the examples is generally more appropriate for laboratory procedures than for large scale production. For large scale operations, it is likely that a flow cell would be used, similar to that in some of the illustrative examples, with a narrow gap between electrodes separated by a membrane divider, and separate catholyte and anolyte streams flowing past their respective electrodes. Further description of suitable cells can be found in the above referenced Organic Electrochemistry, noting particularly Chapter 5 on Practical Problems in Electrolysis, and Chapter 30 on Industrial Electroorganic Chemistry, which describes several commercially used electrolysis cells. When a divided cell is used, it is possible to employ the same electrolysis medium on both the cathode or anode sides, or to employ different media.

In the present process, the reactants and electrolytes can be used over broad concentration ranges as found convenient. Electrolyte salts will generally be provided in amounts for acceptable conductivity and solubility, in amounts for example from about 0.02 molar up to about 0.5 molar, or the limit of solubility. Similarly, the p-isobutylacetophenone can be used in amounts as low as convenient for efficient handling up to the solubility limit, or for example from about 0.02 molar up to about 0.4 molar or so. If desired, the solubility limits can be exceeded for the salts or the ketone reactant, but it will generally be convenient to utilize an essentially single phase reaction medium.

In effecting the electrolysis, current is applied to the cell and the proper cathode voltage is obtained due to the discharge characteristics of the isobutylacetophenone in the reaction system. If desired, the discharge voltage can also be regulated by appropriate electrical means, but that is not necessary. The relationship of isobutylacetophenone quantities to carbon dioxide concentration has some effect on results but good results can be obtained over substantial ranges of these components. A stream of carbon dioxide can be conveniently conducted through the catholyte, possibly providing amounts at or above or below saturation, but other amounts of carbon dioxide can be employed, using above atmospheric pressures if desired. The electrolysis can be conducted at usual current densities for such procedures, with ranges of above 25 to 150 or so milliamperes per square centimeter being convenient in laboratory procedures. In general, for efficient use of current, the current density will be chosen so as not to exceed the mass transfer rate of the component to be reduced at the electrode. In large scale operations, the appropriate current density can be selected in accord with overall economics of the production process, as discussed in Chapter 30 of the above-referenced Organic Electrochemistry, possibly using currents in the 10–100 amperes per square decimeter range described there. The text is of further interest for its discussion of electrolytes and solvents for electrolysis, e.g. at page 205 noting that for reductions dimethylformamide has a usable potential range comparable to acetonitrile. Additional useful information on electrolysis conditions can be found in commonly assigned U.S. Pat. Nos. 4,404,069 to Goodin et al and 4,356,317 to Coleman et al. The teaching of these patents, along with that of Organic Electrochemistry, Experimental Electrochemistry for Chemists, U.S. Pat. No. 4,028,201 and Pat. No. 3,193,480, all referenced hereinabove, is incorporated herein by reference; attention is particularly directed to aspects concerning electrolysis in non-aqueous, aprotic solvent systems.

The present process can be effected at ambient temperatures, or at higher or lower temperatures, e.g. from 0° to 50° C. or higher, as found convenient. Use of low temperatures in this type of reaction may have a moderate influence in improving results, but this is offset by the potential added costs in employing refrigeration means to achieve low temperatures. Some cooling means may be indicated to offset the heat generated by electric current, such as cooling sufficient to maintain near ambient conditions.

As described hereinabove, product recovery is facilitated when a dissolving anode is used. In procedures not using such anodes, the electrolysis product in the present process can be recovered employing usual recovery procedures. Such procedures in general involve a combination of distillation and extraction procedures. Thus the solvent, such as acetonitrile or dimethylformamide, can be stripped off by distillation and the residue can be treated with water, acidified and extracted with an organic solvent, such as diethyl ether, to remove the product from the electrolyte salts, and isolated by stripping the solvent. The acidification step facilitates the separation by ether extraction. After the ether is removed by distillation or evaporation, the product can be refined by crystallization, as by crystallizing from n-hexane. The crystallization from hexane serves to separate the product from unreacted p-isobutylacetophenone and p-(p-isobutylphenyl)-ethanol, or other byproducts, which may be present and remain in the hexane solution. The hydroxyibuprofen can also be separated from these or other organic components by procedures in which the hydroxyibuprofen or its precursors are converted into salt from soluble in aqueous media, and the organics are extracted from an aqueous medium with an organic solvent, while the product salts remain in the aqueous medium for later separation by acidification and extraction. Thus one can separate solvent from the catholyte and treat the residue with aqueous sodium hydroxide, extract the aqueous solution with diethyl ether, then acidify the aqueous solution and extract the hydroxyibuprofen therefrom with diethyl ether. With suitable concentrations, it is also possible to precipitate the hydroxyibuprofen directly from aqueous solution by acidifying the solution.

EXAMPLE 1

An H cell was used for electrolysis, being constructed of two parts from glass, joined at ground surfaces, with a membrane cemented between with a silicone rubber sealant. A Nafion membrane was used, being a permselective membrane of sulfonated fluorocarbon polymer, designed to permit selective passage of cations. The cathode compartment had an effective working volume of about 400 ml, and the anode compartment, about 100 ml. The anode was a ¼ inch, (0.62 cm) diameter graphite rod and the cathode was an Hg pool with 7 cm diameter. The cathode compartment was fitted with a thermowell, overhead stirrer, gas inlet tube and gas exit tube. Power was supplied to the electrodes by direct current from a constant current/voltage power supply (Sorensen DCR150-2.5A). The gas inlet tube was adapted to permit constant supply of carbon dioxide below the surface of the catholyte. A saturated calomel refence electrode was also included. The catholyte was a 400 ml quantity of acetonitrile containing 10 grams 4-isobutylacetophenone and 10 grams tetrabutylammonium bromide, and saturated with carbon dioxide, admitted by the gas inlet tube. The anolyte contained 100 ml acetonitrile and 33 grams tetrabutylammonium bromide, along with 20 ml cyclohexene, which was included as an optional component to scavenge bromine generated at the anode. Electrolytic reaction conducted at 170 milliamperes constant current for about 13 hours with high cell resistance being reached. A low current was employed for a few more hours. The electrolysis was monitored by an Apple/Isaac computer system. A total of 9606 coulombs was passed. A small sample of catholyte was treated with method iodide and used for gas chromatographic mass spectral analysis, showing the methyl ester of the desired 2-hydroxy-2(p-isobutyl-phehyl)propionic acid, along with the starting 4-isobutylacetophenone and p-isobutylphenylethanol. The solvent was stripped from the remainder of the catholyte and the residue was treated with water and extracted with petroleum ether. The aqueous layer was acidified with sulfuric acid, extracted with diethyl ether and the extracts dried over $MgSO_4$ and stripped to a solid, 4 grams. Gas chromatography indicated the solid to be 83% the desired 2-hydroxy-2-(p-isobutylphenyl)-propionic acid. The material was dissolved in hexane and treated while hot with decolorizing carbon and filtered while hot. Upon cooling, solid white crystals were obtained, 1.85 grams. (Some material was lost in the heating procedure). The material had a melting point of 105°-106° C., and there was no depression of the melting point when mixed with an authentic sample of 2-hydroxy-2-(p-isobutylphenyl)propionic acid, thus confirming its identity. Anal. Calc'd for $C_{13}H_{18}O$, C, 70:27; H, 8.11; Found, C, 71.14, 71.07; H, 8.44, 8.45.

In the gas chromatography procedures herein, hydroxyibuprofen and isobutylphenylethanol were generally silated with Regisil ® silation material prior to analysis. Also in the flow system electrolyses, bibenzyl was generally used as an internal standard in the catholyte for analysis of the catholyte during the electrolysis.

EXAMPLE 2

An electrolysis was carried out as in Example 1 but utilizing a graphite rod cathode of ½ inch (1.27 cm) diameter, positioned for immersion of about 6 cm in the catholyte. The catholyte was about 0.1 molar tetrabutylammonium bromide with 10 ml p-acetylisobutylbenzene, and the anolyte was 30 grams of the tetrabutylammonium salt in 100 ml acetonitrile, with 10 ml cyclohexane. Electrolysis was conducted at 200 milliamperes most of the time for 18 hours. Solvent was stripped from the catholyte by distillation. A sample was treated with methyl chloride and used for gas chomatographic mass spectral analysis which showed the methyl ester of 2-hydroxy-2-(p-isobutylphenyl)propionic acid to be present in a ratio of 1 part to 1 part of the starting p-acetyl isobutylbenzene and 0.25 part 1-(p-isobutylphenyl)ethanol. The catholyte residue was treated with water, made basic with NaOH, and extracted with petroleum ether and ether, neither of which would dissolve a brown oil, present in 9.6 gram amount. Gas chromatographic analysis of a sample of the oil showed tributylamine and the butyl ester of 2-hydroxy-2-(p-isobutylphenyl)-propionic acid. The aqueous solution remaining after the extractions was acidified and extracted with diethyl ether, the ether solution was dried over $MgSO_4$, and the ether stripped to have 2.1 grams crude solid product. The previous petroleum ether-ether extract was stripped to 7.3 grams oil, which was added to water, acidified with hydrochloric acid, extracted with ether, and added to the other solid product. The ether was stripped off leaving about 4 grams solid which represents approximately a 30% current efficiency to the hydroxyibuprofen.

An electrolysis similar to that of Example 2 was carried out, but utilizing an aqueous anolyte containing 150 ml water and 10 grams NaOH. A mercury cathode was used. Solid white material was observed in the catholyte. Removal of solvent from the catholyte, followed by treatment with aqueous alkali and ether extraction and removal left a solid material which appeared to be a dimer derivative of the isobutylacetophenone. Acidification of the aqueous alkali solution, followed by ether extraction and removal left very little residue, which was not further treated to determine the desired product therein. A similar procedure but employing a graphite rod cathode, and 5% water in the catholyte, rather than aqueous anolyte, caused extensive cathode corrosion or erosion, and only a pinacol-type dimer was identified as product.

EXAMPLE 3

An electrolysis was run as in Example 1 with 10 grams p-acetylisobutylbenzene but utilizing a graphite rod cathode and acetonitrile catholyte saturated with carbon dioxide and methyl chloride. After electrolysis, treatment of the catholyte with water and use of ether extraction for product separation produced an oil. The mass by mass spectrometry and the NMR values were consistent with the methyl ester of an isomer of hydroxyibuprofen, methyl 2-(p-isobutyl-phenyl)propiocarbonate. The material was distilled under reduced pressure, with a fraction being obtained at 78°-88° at less than 0.1 mm Hg, 3.87 grams. A smaller amount of the methyl ester of hydroxyibuprofen was also present.

EXAMPLE 4

An electrolysis was conducted as in Example 1, but employing a Raipore 4010 membrane as divider, a cation exchange membrane of sulfonated styrene grafted on a fluorinated polymer film. Product separation by aqueous and ether extraction produced an ether extract which gas chromatographic analysis showed to contain the tetrabutylammonium salt of hydroxyibuprofen, the starting ketone reactant and its corresponding alcohol, along with dimers. A similar procedure was conducted but with tetraethylammonium chloride salt, resulting in no product identification when work was stopped. It appeared that the salt contained water and interfered with the reaction. The salt is known to be difficult to obtain in dry condition.

EXAMPLE 5

An electrolysis was conducted in a resin flask with 100 ml of acetonitrile and 5 ml p-acetylisobutylbenzene, and employing 0.03 moles of a quaternary ammonium oxalate salt as electrolyte. A lead cathode faced a graphite rod anode, and electrolysis was run at 140 milliamperes constant current with carbon dioxide saturating the electrolysis solutions. After about 2500 coulombs had passed, gas chromatography showed very little carboxylation product. Alumina was added to the solution to take up water, and electrolysis was continued until 4560 coulombs had passed. Gas chromatography evidenced more of the desired hydroxyibuprofen product, but the product was mostly dimer. Evidently the oxalate salt contained moisture. A similar procedure with an undivided cell using a quaternary ammonium formate salt as electrolyte produced more of the hydroxyibuprofen, but there was still difficulty from moisture in the salt.

EXAMPLE 6

An electrolysis was run as in Example 1 but using a Raipore cation exchange membrane and dimethylformamide (DMF) solvent. The DMF was stripped from the catholyte and the residue was treated with 400 ml water and extracted with petroleum ether. The aqueous phase was acidified with hydrochloric acid, extracted with ether and the ether was dried over $MgSO_4$ and stripped to leave a mushy solid, 9.7 grams. Recrystallization from hexane gave 4.5 grams of hydroxyibuprofen, compared to the theoretical yield of 7.4 grams, a 61% yield of the recrystallized product. A similar procedure was run using a graphite rod cathode. After the electrolysis, the catholyte was stripped of solvent and the residue added to water, which was acidified with HCl, extracted with ether and the ether stripped to an 11.2 gram residue. Gas chromatographic analysis showed it was 56.5% hydroxyibuprofen and 16.8% the starting ketone. This indicated 6.32 grams of the hydroxyibuprofen for approximately a 78% yield, based on the ketone utilized, i.e. not in the product. A similar procedure utilizing a lead cathode produced about a 58% yield of hydroxyibuprofen.

EXAMPLE 7

A typical plate and frame cell was utilized, having a Nafion permselective membrane between a lead cathode and a graphite anode, with plastic spacers between the membrane and the electrodes. The spacers were cut to expose 8 sq. cm. of the electrodes. Ports were provided for solution flow between the membrane and the respective electrodes, with connection by Teflon fluorinated polymer tubing to pumps and catholyte and anolyte reservoirs. The catholyte was 250 ml acetonitrile containing 8 grams tetrabutylammonium bromide and 10 grams p-isobutylacetophenone. Carbon dioxide to saturate the catholyte was introduced just upstream of the inlet to the cathode compartment. The anolyte was 250 ml acetonitrile containing 30 grams tetrabutylammonium bromide and 15 ml cyclohexene. The electrolysis was run at 280 milliamperes for 9 hours, with approximately a 7 volt cell voltage. The coulomb passage was 9072. Acetonitrile was stripped from the catholyte and the residue was treated with water, acidified with concentrated hydrochloric acid, and extracted with ether. The ether was dried over $MgSO_4$ and stripped to a semisolid, 11.14 grams. Assay showed 51.5% hydroxyibuprofen, 16.3% isobutylphenylethanol and 22.1% isobutylacetophenone. This represents a 60% yield of hydroxyibuprofen, based on unrecovered starting material. The current efficiency, based on isobutylacetophenone reacted, was 91%. A repetition at twice the current density, 100 milliamperes/sq.cm., gave a chemical yield to hydroxyibuprofen of 46%, and a 70% current efficiency on isobutylacetophenone reacted. The yield of isobutylphenylethanol was 45%.

EXAMPLE 8

An electrolysis was run as in Example 7 at 50 milliamperes/sq.cm. After passage of 10381 coulombs, the catholyte was worked up to obtain 16.7 grams product, with 5.97 grams hydroxyibuprofen content representing a 56.4% yield. Sample analysis during the electrolysis had shown hydroxyibuprofen yields of 67 to 78% and current efficiencies (on isobutylacetophenone utilized) from 69 to 75%, but this is at variance with the final product assay.

EXAMPLE 9

An electrolysis was run as in Example 7 but utilizing 15 grams p-isobutylacetophenone and DMF as solvent. Bibenzyl was used in the catholyte as an internal standard. The current was maintained at 400 milliamperes with a cell voltage of about 20 volts. By water and acid treatment and ether extraction, a 23.12 gram oil product was obtained, which was assayed as containing 8.28 grams hydroxyibuprofen, 0.236 gram isobutyl-phenylethanol and 5.18 grams of the isobutylacetophenone starting material, representing a 67% yield of the hydroxyibuprofen. However, samples analyzed by gas chromatography during the electrolysis showed yields of hydroxyibuprofen varying from 88.6% to 74%. A similar electrolysis but at 100 milliamperes/sq. cm. resulted in a 24.4 gram crude product assaying as 8.13 grams hydroxyibuprofen, 0.5 gram isobutylphenylethanol and 4.8 grams p-isobutylacetophenone. Mass balance was 78%. Gas chromatographic analysis of samples during the electrolysis indicated hydroxyibuprofen yields of 41 to 61%. A repeat of the electrolysis, but with lithium chloride as electrolyte, led to very little or no hydroxyibuprofen product. Extensive corrosion of the lead electrode was evident.

EXAMPLE 10

An electrolysis was run as in Example 7, except the electrodes were carbon felt bonded to graphite, providing high surface area. The electrolysis was run at 400 milliamperes for 11200 coulombs. Some solid formation in the catholyte was observed. Sample analysis during the electrolysis indicated a poor yield in the first sample and then yields of hydroxyibuprofen in the 40 to 60% range. The electrolysis was repeated but using 25 grams of p-isobutylacetophenone in the catholyte, for higher reactant concentration. Current was 400 milliamperes at approximately 7.5 volt cell voltage. Solids quickly appeared in the catholyte. Sampling indicated the p-isobutylacetophenone content declined to 9.3 grams as the hydroxyibuprofen content rose to 11.2 grams at a passage of 27,400 coulombs. Yields of hydroxyibuprofen were in the range of 50 to 65%, being in the 60 to 65% range for a good portion of the electrolysis. The amount of p-isobutylphenylethanol produced was only 1 gram. (The solids formation observed in the catholyte was found to be from sealant used in the cell assembly).

EXAMPLE 11

An electrolysis was run as in Example 9, but the flow cell had a copper cathode and graphite plate anode. The catholyte contained a 15 gram amount of p-isobutylacetophenone and electrolysis was conducted at 400 milliamperes with 18 volt cell voltage. Sampling during the electrolysis indicated hydroxyibuprofen yields of 68 to 85%, with yields of 80–85% much of the time. A total of 16000 coulombs was passed and toward the end of the electrolysis there was some product consumption, the amount of hydroxyibuprofen declining from 8.4 grams to 7.3 grams. Current efficiency, based on isobutylacetophenone reacted, reached levels of 90%, and the amount of isobutylphenylethanol produced did not exceed 0.5 gram. The electrolysis was repeated but using a current of 200 milliamperes. Results were similar, but the hydroxyibuprofen yield was 85–90% at times while current efficiency was somewhat lower, being near 80% much of the time.

EXAMPLE 12

The electrolysis was carried out in a 100 ml resin flask with Hg pool (3.5 cm dia) cathode and Al foil anode. A magnetic stirring bar to stir the solution floated on the Hg surface. Electrical contact to the Hg pool was via a Pt wire sealed in glass. The cell was fitted with a gas inlet tube which extended below the level of the solution and a gas exit tube.

The solution consisted of 100 ml $CH_3CN$, 10 g 4-isobutylacetophenone and 5 g $Bu_4N^+Br^-$. The solution was saturated with $CO_2$ and $CO_2$ was continually bubbled through the solution during the electrolysis.

The electrolysis was run at 150 ma until 7030 coul. had passed. The Al anode partially dissolved. Solid formed in the solution shortly after the electrolysis was begun. After the electrolysis was stopped, the solid was filtered from the solution. The solid (presumably the aluminum salt of products (and byproducts)) was treated with dilute sulfuric acid and then that solution was extracted with ether. The ether extract was dried over $MgSO_4$ and stripped to a residue (6.5 g) which was analyzed to be roughly ⅓ hydroxyibuprofen, ⅓ pinacol typedimer and ⅓ isobutylphenylethanol.

EXAMPLE 13

An electrolysis was carried out in an undivided cell as in Example 12, except that an iron anode was substituted for the aluminum anode. The electrolysis was run at 150 ma until 12300 coulombs had passed. A dark solid formed in the electrolysis mixture. At the end of the electrolysis the solution was filtered (very difficult to filter) to remove product in the form of iron salts. The solid was treated with aqueous $H_2SO_4$ and ether. The ether extract was dried over $MgSO_4$ and stripped to an oil (6.4 g). Analysis of the crude product by gas chromatography showed the ratio of products to be 1:1:1.5 for 4-isobutylphenylethanol, hydroxyibuprofen and pinacol type dimer respectively. It was observed that the iron anode had partially dissolved during the electrolysis.

EXAMPLE 14

An electrolysis was run in a cell as described in Example 1 with a mercury pool cathode and graphite rod anode. The catholyte was 350 ml dimethylformamide with 0.1 molar tetrabutylammonium bromide, containing 10 grams 2-acetyl-6-methoxynaphthalene, and it was saturated with $CO_2$. The anolyte was 100 ml dimethylformamide containing 35 grams tetrabutylammonium bromide and 20 ml cyclohexene. Electrolysis was run at 200 milliamperes until 8853 coulombs passed. The anolyte went dry, so the electrolysis was terminated. The cathode potential vs. a saturated calomel electrode was initially −1.82 volts and became somewhat less negative as the electrolysis progressed and the current was reduced. A small sample of the catholyte was removed and treated with methyl iodide and used for a gas chromatographic, mass spectrometer analysis, with identification as the methyl ester of 2-hydroxy(6-methoxynaphthyl-2)propionic acid. The remaining catholyte was stripped on a rotary drier to remove dimethylformamide. The residue was treated with water and extracted with petroleum ether, with some insoluble solid appearing in both phases. The petroleum ether was decanted and the remaining aqueous solution was extracted with ether and acidified with $H_2SO_4$, causing an oil to separate, which was then extracted with ether. The ether extract was dried over $MgSO_4$ and the ether was stripped. The 6.5 gram residue was washed with ether, and indicated as 2-hydroxy-2-(6-methoxynaphthyl-2)propionic acid by its melting point, 166°–167° C., compared to 167°–168° C. in U.S. Pat. No. 4,188,491. The NMR and elemental analysis were consistent with the identification. The product can be hydrogenolyzed to the therapeutic product, naproxen.

EXAMPLE 15

Electrolysis was conducted employing a cell as in Example 1 with a mercury pool cathode and graphite rod anode. The catholyte was 300 ml 0.1 molar tetrabutylammonium bromide in dimethylformamide with 15 grams 2-acetylfluorene which was kept saturated with carbon dioxide. The anolyte was 30 grams tetrabutylammonium bromide in 100 ml dimethylformamide, with 10 ml cyclohexene. The cell was cooled by a water bath, and provided with current control and computer monitoring as in Example 1. Electrolysis was run at 250 milliamperes with an initial cathode potential of −1.78 volts vs. saturated calomel electrode, and then at 150 milliamperes overnight. The anolyte went dry and a total of 13310 coulombs passed. The catholyte was stripped on a rotary evaporator. The mushy residue was treated with 500 ml water and extracted with ether to give two dark green phases. The aqueous phase was acidified with $H_2SO_4$ and turned yellow with precipitation. The solid was separated by filtration and recrystallized from toluene. A sample of the material was silated and gas chromatography mass spectrometry identified it as 2-hydroxy-(2-fluoryl)propionic acid. NMR analysis was consistent with this product, and also showed a large amount of tetrabutylammonium cation. The solid was stirred with chloroform to remove the cation and recrystallized from methanol. The product had a melting point of 173°–175° C., compared to a literature melting point of 176°–178° C. for 2-hydroxy-(2-fluoroyl)propionic acid (E. J. Stiller et al., J. Med. Chem., 15, 1029 (1972). The elemental analysis was consistent with the assigned structure. The product can be hydrogenolyzed to the therapeutic product, cicloprofen.

EXAMPLE 16

The electrolysis of Example 15 can be repeated under the same general conditions with other selected substituted aryl methyl ketones, with expected hydroxypropionic acid products to be produced as follows:

The compound 2-isopropyl-5-acetylindane will produce 2-isopropyl-α-hydroxy-α-methylindane-5-acetic acid (reported melting point 140°–143° C., J. Med. Chem. 21, 901 (1978).

The compound 2-fluoro-4-acetylbiphenyl will produce 2-(2-fluoro-4-biphenyl)-2-hydroxypropionic acid (reported melting point 166°–169° C., U.S. Pat. No. 4,304,931).

The compound 3-acetyldiphenyl ether will produce 2-(3-phenoxyphenyl)-2-hydroxy propionic acid (reported melting point 99°–100° C., U.S. Pat. No. 4,188,491).

The compound 2-acetyl-6-chlorocarbazole will produce 6-chloro-α-hydroxy-α-methyl carbazole-2-acetic acid (reported melting point 218°–220° C., U.S. Pat. No. 4,150,031).

The products obtained in Example 16 can be hydrogenolyzed to obtain the corresponding therapeutic compounds, namely, isoprofen, flurbiprofen, fenoprofen, and carprofen.

EXAMPLE 17

For hydrogenolysis, a 0.44 gram amount of 2-hydroxy-2-(p-isobutylphenyl)propionic acid was placed in a glass-lined Parr Bomb with 60 mg of an acidic ion exchange resin comprised of polystyrene with sulfonate groups sold under the mark Amberlyst ® 15, 0.15 ml acetic anhydride and 10 ml acetic acid, and 42.5 mg of a 5% by weight palladium on carbon catalyst. The bomb was flushed with hydrogen and pressured to 100 psi (694.74 KPa) gauge and placed in a 100° C. oil heater for 18 hours, with a 30 psi (206.84 KPa) gauge uptake of hydrogen being measured, and a temperature of 104° C. The product solution was silated and analyzed by gas chromatography with a strong peak for 2-p-isobutylphenylpropionic acid being present and very little of the starting 2-hydroxy-2-(p-isobutylphenyl)propionic acid. Some unidentified material was also present.

I claim:

1. A process of preparing a carboxylation product convertible to a 2-aryl-2-hydroxypropionic acid by treatment with acid which comprises electrolyzing at at cathode an aryl methyl ketone in the presence of carbon dioxide in an electrolysis medium comprising organic solvent and supporting electrolyte to effect addition of carbon dioxide to the aryl methyl ketone, with the aryl group being selected from p-isobutylphenyl, 6-chlorocarbazyl-2, 3-phenoxyphenyl, 2-isopropylindanyl-5, 2-fluoryl, 2-fluoro-4-biphenylyl, and 6-methoxynaphthyl-2.

2. The process of claim 1 in which the cathode voltage is sufficiently negative to effect reductive carboxylation of the aryl methyl ketone.

3. The process of claim 1 in which the acid is used to effect conversion of the carboxylation product to the acid form.

4. The process of claim 1 in which the electrolysis is carried out in an aprotic solvent medium containing a quaternary ammonium salt.

5. The process of claim 1 in which a divided cell is used.

6. The process of claim 1 in which a divided cell is used containing a membrane divider which selectively passes cations.

7. The process of claim 6 in which the process is carried out in an aprotic solvent medium containing a tetrabutylammonium salt.

8. The process of claim 1 in which an anode which dissolves during the electrolysis is employed and product salt of anode metal precipitates during the electrolysis.

9. The process of claim 8 in which product salt is filtered from electrolyte medium which still contains electrolyte salt.

10. The process of claim 9 in which an undivided cell is used.

11. The process of claim 1 in which 4-acetylisobutylbenzene is converted to a carboxylation product convertible by acid to 2-hydroxy-2-(p-isobutylphenyl) propionic acid.

12. The process of claim 11 in which cathode voltage is sufficiently negative to effect reductive carboxylation of the 4-acetylisobutylbenzene.

13. The process of claim 11 in which acid is used to effect conversion of the carboxylation product to the acid form, 2-hydroxy-2-(p-isobutylphenyl)propionic acid.

14. The process of claim 8 in which the aryl group is p-isobutylphenyl.

15. The process of claim 1 in which 2-acetylfluorene is converted to 2-hydroxy-2(fluoryl-2-)propionic acid.

16. The process of claim 1 in which 2-acetyl-6-methoxynaphthalene is converted to 2-hydroxy-2-(6-methoxynaphthyl-2)propionic acid.

17. The process of claim 1 in which the product is hydrogenolyzed to the corresponding arylpropionic acid.

18. The process of claim 1 in which carboxylation product is obtained in salt form due to presence of salt cation in the electrolysis medium.

19. The process of claim 1 in whichan alkyl halide is provided to effect conversion of the carboxylation product to ester form.

20. The process of claim 11 in which carboxylation product is obtained in salt form due to presence of salt cation in the electrolysis medium.

21. The process of claim 11 in which an alkyl halide is provided to effect conversion of the carboxylation product to ester form.

* * * * *